(12) United States Patent
Gilliam et al.

(10) Patent No.: US 8,727,185 B2
(45) Date of Patent: May 20, 2014

(54) DISPENSER DEVICE AND SYSTEM

(75) Inventors: Michael Gilliam, Coral Springs, FL (US); Rafael A. Martinez, Boca Raton, FL (US)

(73) Assignee: GM Ergonomics, LLC, Boca Raton, FL (US)

( * ) Notice: Subject to any disclaimer, the term of this patent is extended or adjusted under 35 U.S.C. 154(b) by 0 days.

(21) Appl. No.: 13/343,359

(22) Filed: Jan. 4, 2012

(65) Prior Publication Data

US 2013/0168417 A1 Jul. 4, 2013

(51) Int. Cl.
*B67D 7/60* (2010.01)
*G01F 11/00* (2006.01)

(52) U.S. Cl.
USPC .......................... 222/391; 222/137; 222/327

(58) Field of Classification Search
USPC ........... 222/135, 391, 145.1, 145.6, 327, 136, 222/137
See application file for complete search history.

(56) References Cited

U.S. PATENT DOCUMENTS

| | | | |
|---|---|---|---|
| 3,311,265 A | 3/1967 | Creighton, Jr. et al. | |
| 4,340,367 A | 7/1982 | Vadas et al. | |
| 4,366,919 A | 1/1983 | Anderson | |
| 4,538,920 A | 9/1985 | Drake | |
| 4,995,540 A | 2/1991 | Colin et al. | |
| 5,033,650 A | 7/1991 | Colin et al. | |
| 5,064,098 A | 11/1991 | Hutter, III et al. | |
| 5,104,005 A * | 4/1992 | Schneider et al. | 222/137 |
| 5,137,181 A * | 8/1992 | Keller | 222/134 |
| 5,184,757 A * | 2/1993 | Giannuzzi | 222/82 |
| 5,242,082 A * | 9/1993 | Giannuzzi | 222/82 |
| 5,314,092 A * | 5/1994 | Jacobsen et al. | 222/137 |
| 5,722,829 A * | 3/1998 | Wilcox et al. | 433/90 |
| 5,755,362 A * | 5/1998 | Rodriguez et al. | 222/391 |
| 5,992,694 A * | 11/1999 | Keller | 222/137 |
| 6,173,869 B1 | 1/2001 | Thayer | |
| 6,182,867 B1* | 2/2001 | Keller | 222/137 |
| 6,585,696 B2* | 7/2003 | Petersen et al. | 604/191 |
| 2001/0013526 A1* | 8/2001 | Keller | 222/327 |
| 2011/0095054 A1* | 4/2011 | Hughes | 222/137 |

OTHER PUBLICATIONS

Miltex, Inc., Traqlig Syringe, www.dentalproductshopper.com/n-tralig-syringe (Oct. 4, 2011).

* cited by examiner

*Primary Examiner* — Paul R Durand
*Assistant Examiner* — Jeremy W Carroll
(74) *Attorney, Agent, or Firm* — Duane Morris LLP; J. Rodman Steele, Jr.; Gregory M. Lefkowitz

(57) ABSTRACT

A dispensing device is described. The dispensing device can include a body comprising a downwardly extending, elongated handle, at least one plunger slidably coupled to the body, and a trigger pivotably coupled to the body at a pivot point. The trigger can include a trigger portion extending downward from the pivot point and a transfer arm extending above the pivot point. The dispensing device can also include an actuator for engaging and advancing the at least one plunger in an axial direction and an elongated linkage extending axially and transmitting motion from the transfer arm to the actuator. The actuator can be positioned behind the handle and the linkage can cause the actuator to move forward axially when the trigger portion is pulled.

18 Claims, 12 Drawing Sheets

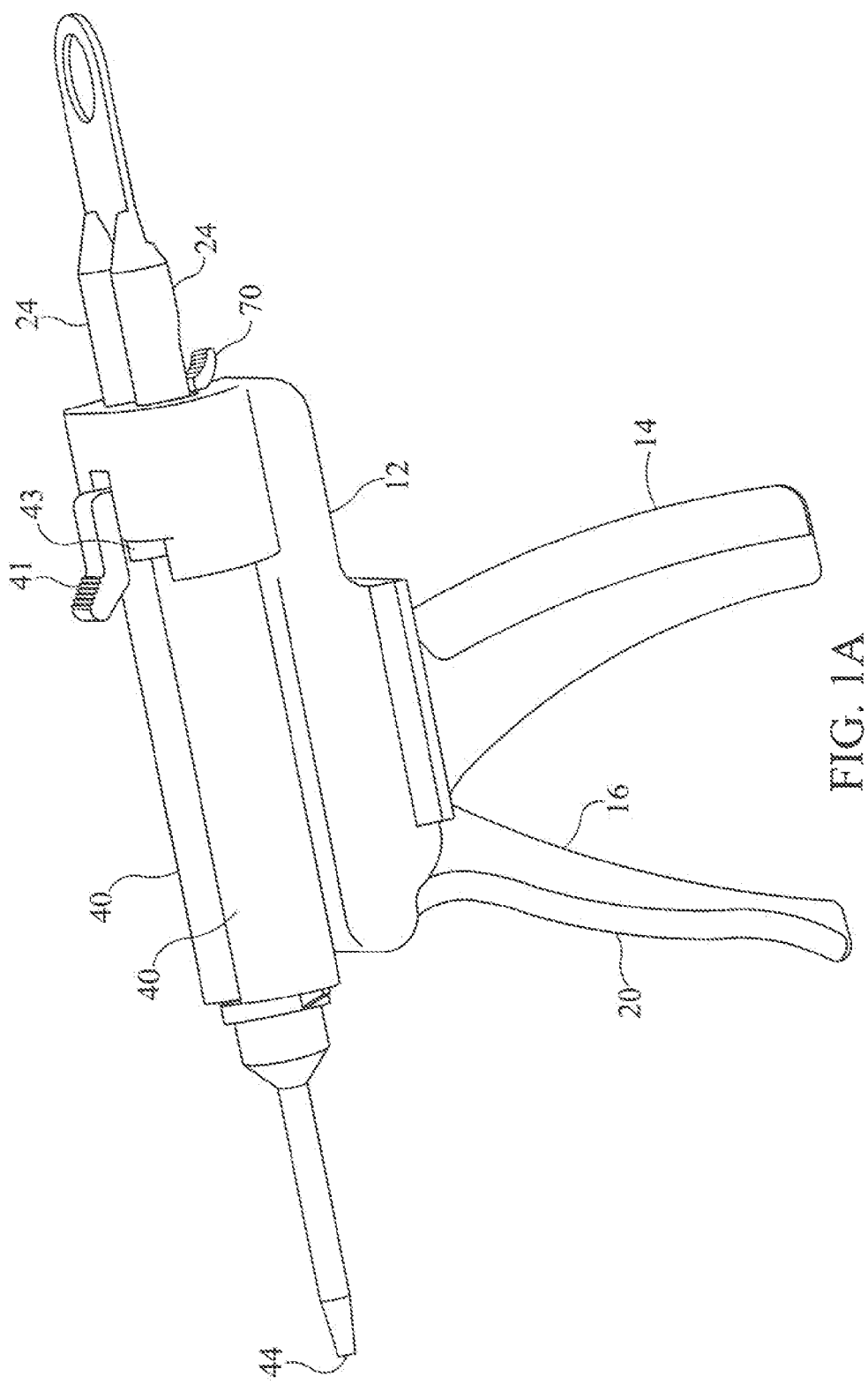

DISPENSER DEVICE AND SYSTEM

FIELD OF THE INVENTION

The present invention relates generally to a dispensing device, particularly, a dispensing device for dispensing viscous fluids—such as bi-phase materials for dental procedures—from a cartridge.

BACKGROUND

Devices for dispensing curable materials, such as caulk, epoxy, etc., from cylindrical cartridges that are removably attached to the devices are well-known. Such devices can be used in a wide variety of applications, but are probably best known for their applications in construction for dispensing caulk and other sealant materials. However, they are also used to dispense materials, such as the bi-phase materials used in a variety of dental and orthopedic surgical procedures, as well as, specialized construction applications.

Bi-phase material dispensing devices are ubiquitous to dental procedures. However, existing bi-phase dispensing devices suffer from a long list of deficiencies, which has led to some dentists to dispense the bi-phase materials from the cylindrical cartridges into a secondary syringe. Because the bi-phase materials begin curing immediately after being discharged from the cartridges into the secondary syringe, this approach has numerous drawbacks, including insufficient capacity of the secondary syringes, time constraints, and wasted syringes and costly bi-phase materials. Accordingly, there is a need for improved devices for dispensing curable materials from cylindrical cartridges.

SUMMARY OF THE INVENTION

Dispensing device for dispensing materials from an elongated cartridge are described. The dispensing device can include a body comprising a downwardly extending, elongated handle and a trigger pivotably coupled to the body at a pivot point. The trigger can include a trigger portion extending downward from the pivot point and a transfer arm extending above the pivot point. The dispensing device can also include at least one plunger slidably coupled to the body and an actuator for engaging and advancing the at least one plunger in an axial direction. The transfer arm and the actuator can be coupled by an elongated linkage extending axially and transmitting motion, e.g., axially, from the transfer arm to the actuator. The linkage can cause the actuator to move forward axially when the trigger portion is pulled.

The at least one plunger can include at least two plungers slidably coupled to the body. The at least two plungers can be coupled to one another in a side-by-side configuration. The elongated linkage can be a rigid linkage.

The actuator can be located behind the handle. The actuator can also be behind the trigger. The trigger can be positioned on the forward side of the handle.

The body can include a housing for receiving the actuator, and the actuator can be slidably coupled to the body. The body and the actuator can be slidably coupled, via a guide and a track.

The at least one plunger can include a ratcheted track and the actuator can include a pawl surface adapted to engage the ratcheted track when the actuator moves forward. The dispensing device can also include a pawl release lever. The pawl surface can disengage from the ratcheted track when the pawl release lever is actuated. A portion of the pawl release lever can extend out of the housing.

In one embodiment, the actuator can include a drive body and a drive insert having a pawl surface. The drive insert can be compressibly coupled to the drive body and can be upwardly biased. A proximal end of the pawl release lever can be pivotably coupled to the body and a distal end of the pawl release lever can include the pawl release tab. An intermediate portion of the pawl release lever can extend through an opening in the drive insert, the drive body, or both.

In another embodiment, the actuator can be generally L-shaped and can include both the pawl release lever and the pawl surface. The pawl release tab can be at a first end of the actuator and the pawl surface can be at the opposite end of the actuator. The generally L-shaped actuator can be pivotably coupled to the linkage between the pawl release tab and the pawl surface. The actuator can be pivotably coupled to the linkage proximate the intermediate corner of the L-shape.

A dispensing system that includes a dispensing device as described herein and at least one elongated cartridge releasably connectable to the device is also described. The dispensing device can include at least two plungers slidably coupled to the body and at least two elongated cartridges. The actuator can be positioned behind the handle.

These and other features, objects and advantages of the present invention will become more apparent to one skilled in the art from the following description and claims when read in light of the accompanying drawings.

BRIEF DESCRIPTION OF THE DRAWINGS

FIG. 1A is a perspective view and FIG. 1B is a side view of a dispensing device as described herein.

FIG. 9B shows the actuator of the second embodiment.

DETAILED DESCRIPTION

Figure 1B:
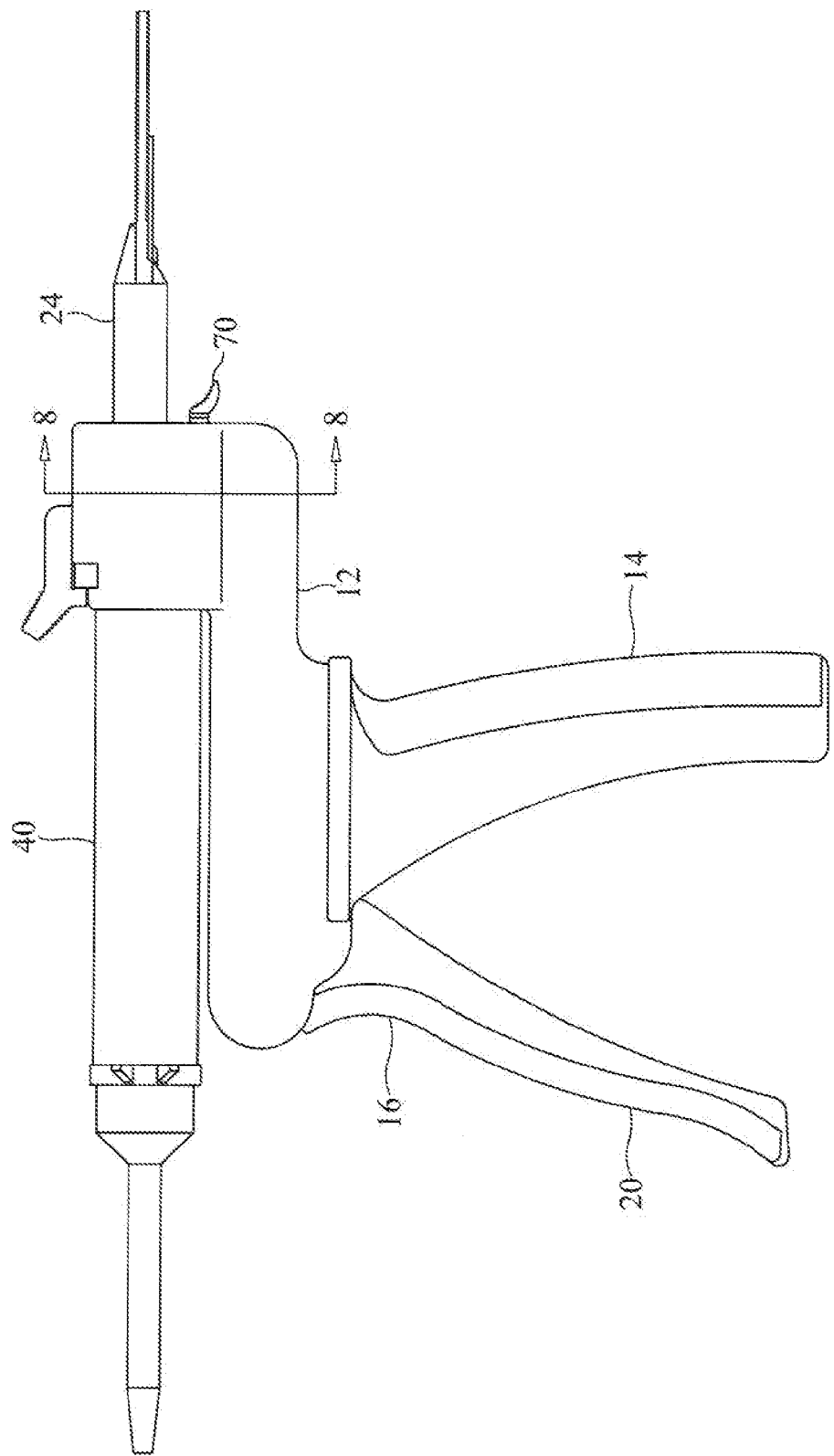

A dispensing device for dispensing a composition from a cartridge removably mountable to the device is described. The dispensing device can be used for dispensing bi-phase compositions, such as those commonly employed in dentistry and orthopedic surgery. A particular benefit of the dispensing devices is that they are designed such that the dispensing end of the cartridges is proximate the front of the dispensing device, which provides the doctor enhanced control when applying the composition during delicate procedures.

As shown in FIGS. 1-11, the dispensing device 10 can include a body 12 having a downwardly extending, elongated handle 14. A trigger 16 can be pivotably coupled to the body 12 at a pivot point 18. The trigger 16 can include a trigger portion 20 extending downward from the pivot point 18 and a transfer arm 22 extending above the pivot point 18. The trigger 16 can be positioned forward of the handle 14.

The dispensing device 10 can include at least one plunger 24 slidably coupled to the body 12 and an actuator 26 for engaging and advancing the at least one plunger 24 in an axial direction when the trigger 16 is actuated, e.g., pulled. The actuator 26 also prevents the plunger 24 from sliding backwards except when desired by the user, e.g., using the pawl release lever 56.

The at least one plunger 26 can include at least two plungers slidably coupled to the body 12. For example, some dispensing devices 10 can be adapted for dispensing bi-phase materials from separate cartridges 40. In such instances, two plungers 24 can be coupled together to dispense the materials from the separate cartridges 40 simultaneously. As shown in FIGS. 1A, 1B, 3, 4 and 10, the plungers 24 can be coupled together in a side-by-side arrangement. Similarly, the removable cartridges 40 can be coupled in, a side-by-side arrangement. The distal end 84 of the coupled plungers 24 can have different diameters in order to dispense different amounts of material from the cartridges 40 of different diameters.

An elongated linkage 28 can extend axially and transmit motion from the transfer arm 22 to the actuator 26. The linkage 28 can cause the actuator 26 to move forward axially when the trigger portion 20 is pulled. The linkage 28 can be formed of a stiffened material so that the actuator 26 is returned to its initial position when the trigger 16 returns to its initial position away from the handle 14. Exemplary stiffened materials include metals, polymers, ceramics, combinations thereof, and other similar materials. The elongated linkage 28, transfer arm 22 and actuator 26 can be positioned within a hollow portion of the body 12.

As used herein, "axially" is used to refer to the direction of movement of the at least one plunger and minor deviations. For example, "axially" can include deviations of ±15°, or ±10°, or ±5° from axial. As used herein, "forward" and "behind" are relative terms and reference a direction generally forward or behind, respectively, a reference position along the axial axis irrespective of the vertical position of the objects.

Figure 2:
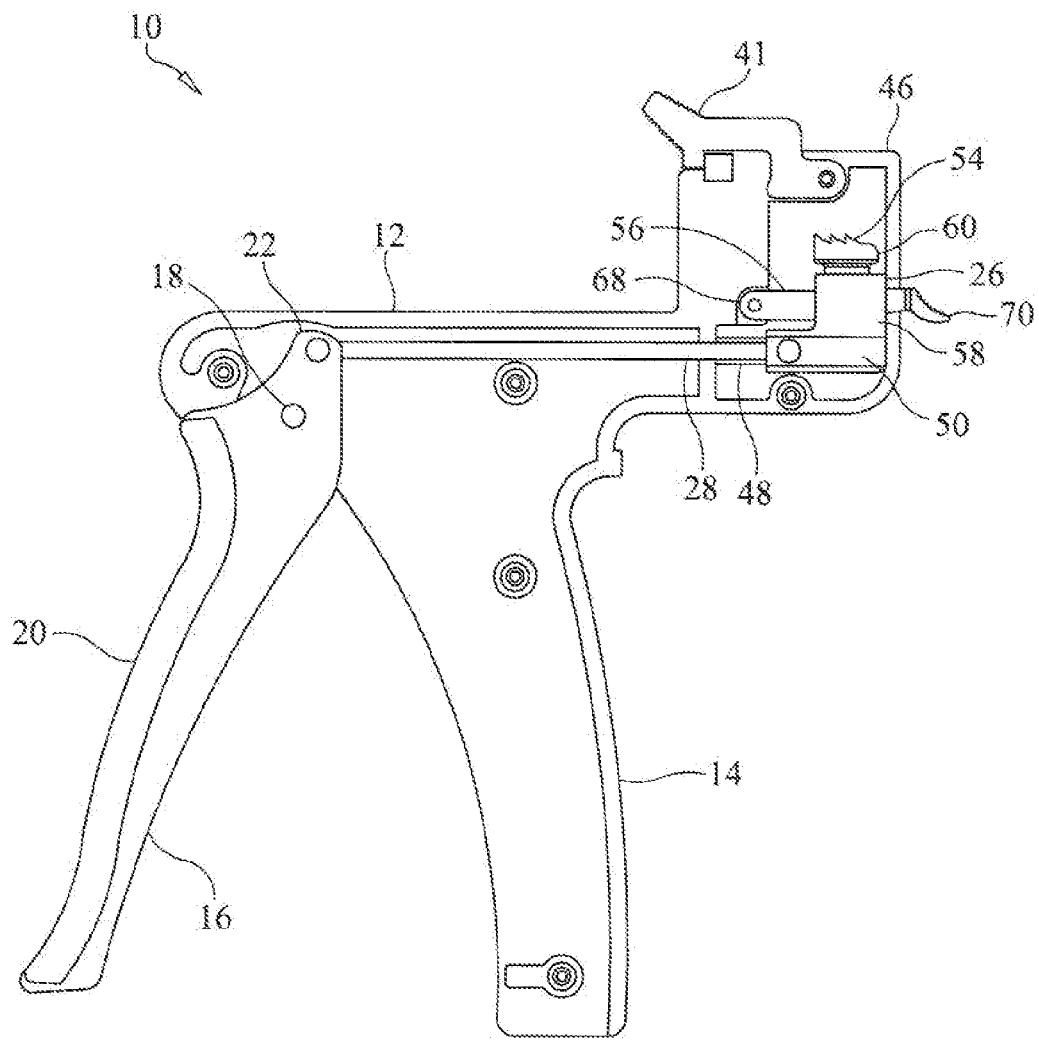
FIG. 2 is a side view of the dispensing device shown in FIG. 1 with a side thereof removed to expose the ratchet actuation mechanism contained within the body.
Figure 3:
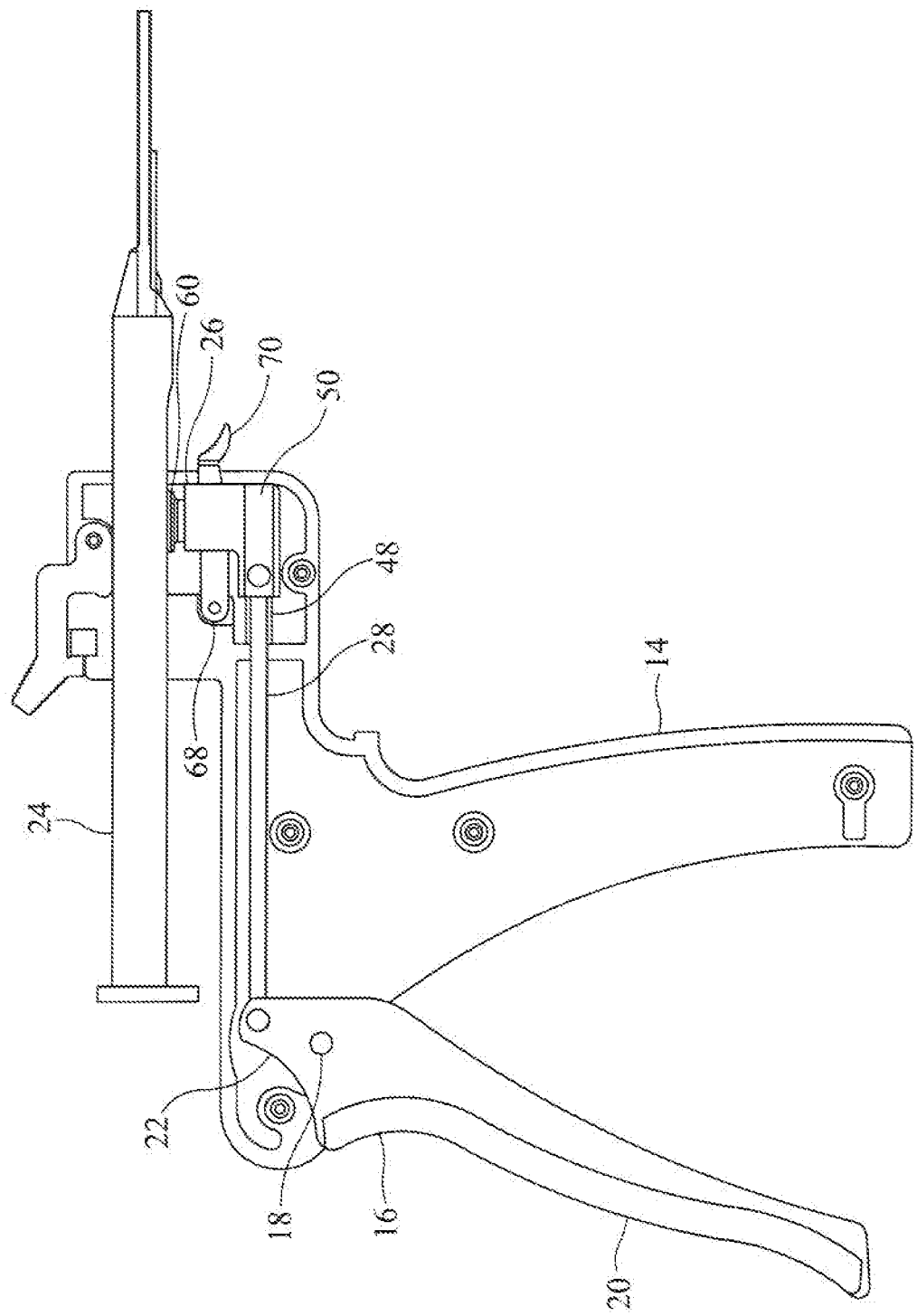
FIG. 3 is a side view of the dispensing device shown in FIG. 1, including a plunger, with a side removed to expose the ratchet actuation mechanism contained within the body.
Figure 4:
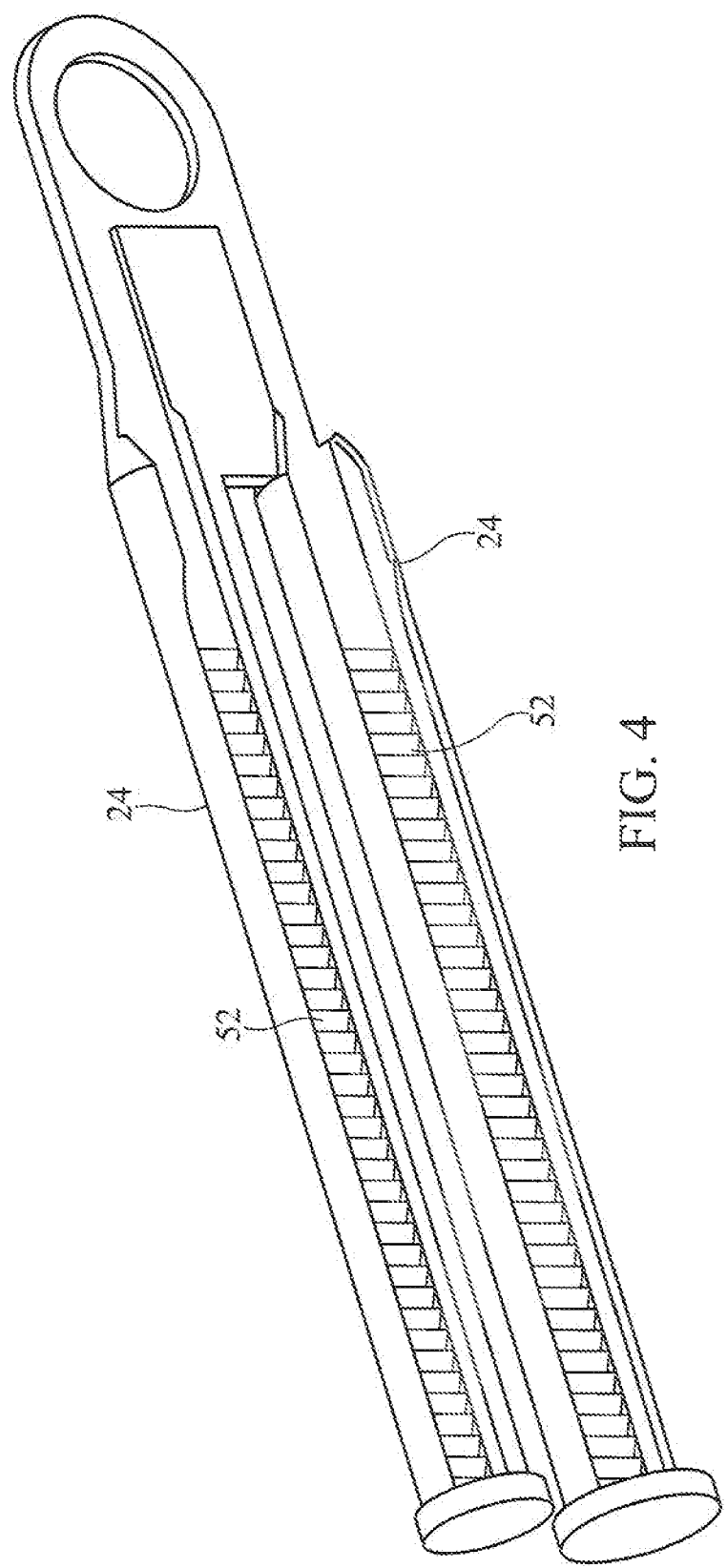
FIG. 4 is a perspective view of a plunger useful in the dispensing devices described herein.
Figure 5:
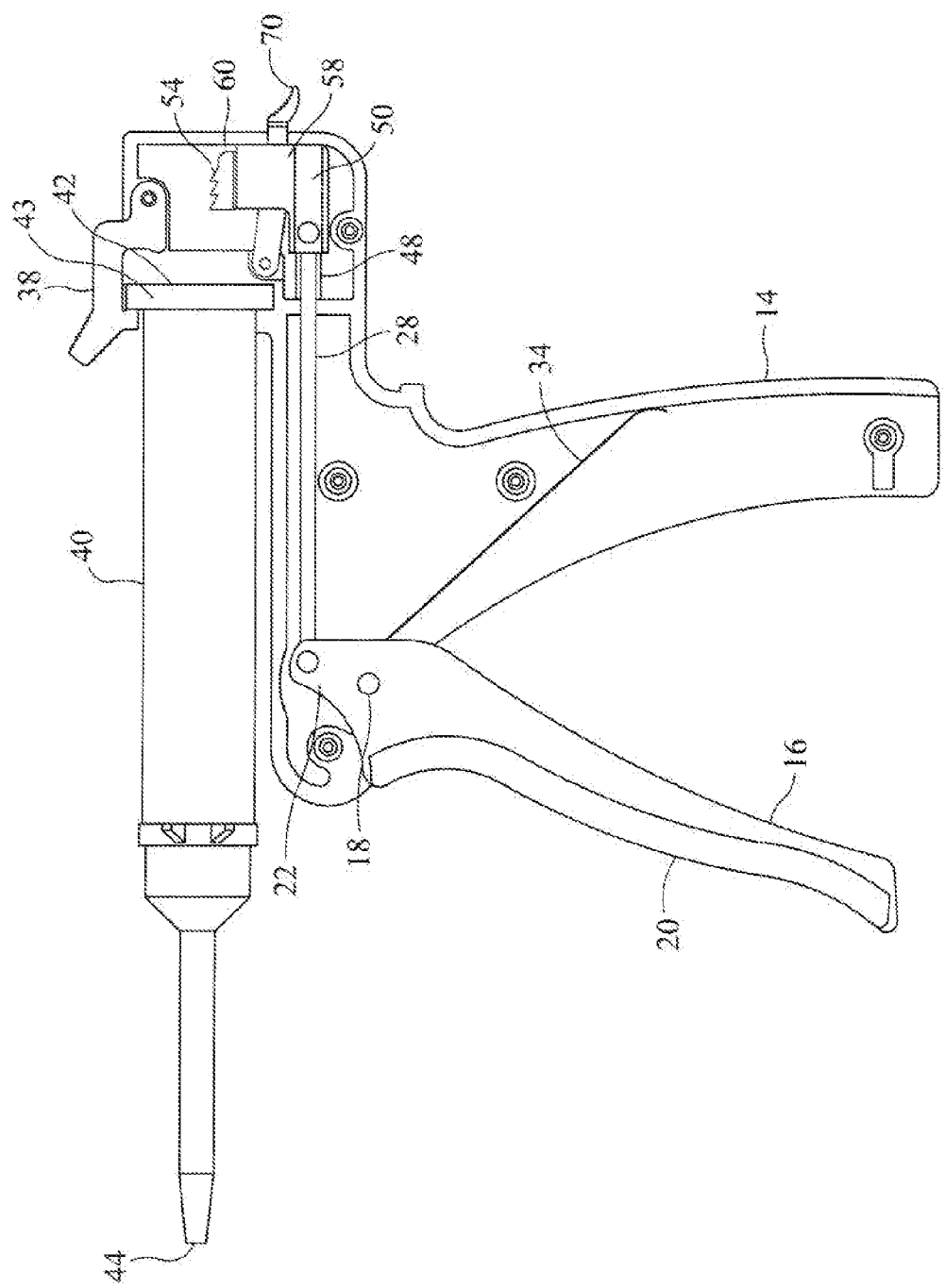
FIG. 5 is a side view of the dispensing device shown in FIG. 1, including an elongated cartridge attached thereto, with a side removed to expose the ratchet actuation mechanism contained within the body.

As used herein, "vertical" refers to an axis perpendicular to the axial axis and extending on the plane of the sheet of FIGS. 1B, 2 and 3. As used herein, "upward" and "downward" are relative terms and reference a direction generally above or below, respectively, a reference position along the vertical axis irrespective of the axial position of the objects.

Figure 6:
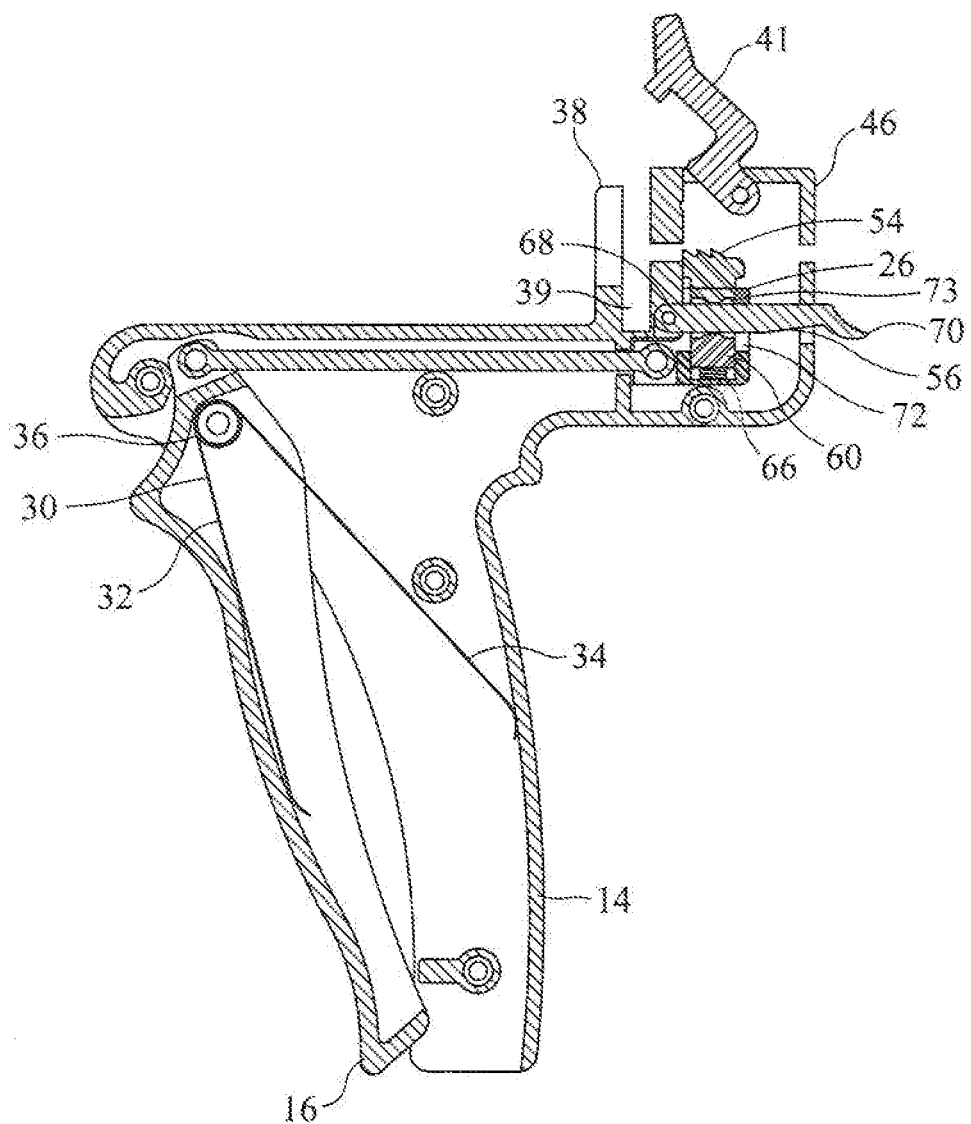
FIG. 6 is a cross-sectional side view of the dispensing device of FIG. 1, with the trigger in the actuated position.

As shown in the Figures, the trigger portion 20 can be positioned forward of the handle 14. The trigger portion 20 can be biased away from the handle 14. For example, a handle spring 30 can be provided to bias the trigger portion 20 away from the handle 14. As shown in FIG. 6, a handle spring 30 can include two opposing arms 32, 34 extending from a coiled portion 36. The coiled portion 36 can be mounted over the pivot point 18 with one arm 32 contacting the trigger portion 20 and the opposite arm 34 contacting the handle 14. The handle spring 30 should be strong enough to force the trigger 16 to the initial position, shown in FIGS. 1A & 1B, following compression by the user. For example, when the user ceases to apply pressure to the trigger 16 the handle spring 30 can return the trigger 16 to its initial position away from the handle.

The dispensing device 10 can also include a cartridge mount 38 for releasably mounting one or more cartridges 40. As shown in the Figures, the cartridge mount 38 can include a receiving channel 39 and a closure clip 41. The closure clip 41 can be pivotably coupled to the body 12, e.g., a forward portion of the housing 46. The cartridges 40 can include a mounting lip 43 located at a proximal end 42 of the cartridge 40. The mounting lip 43 can be configured to fit into the receiving channel 39 for secure, releasable attachment of the cartridge 40.

There can be a plunger 24 for each of the cartridges 40. When the cartridge 40 is attached to the body 14, e.g., via the mounting lip 43, each plunger—cartridge pair can be arrange coaxially so that the plunger 24 extends into the cartridge 40 when the plunger 24 is advanced axially by pulling the trigger portion 20. In this arrangement, the contents of the cartridge 40 are forced out of the tip 44 of the cartridge 40 as the trigger portion is pulled and the plunger 24 advances axially into the proximal end 42 and toward the tip 44 of the cartridge 40.

Figure 8:
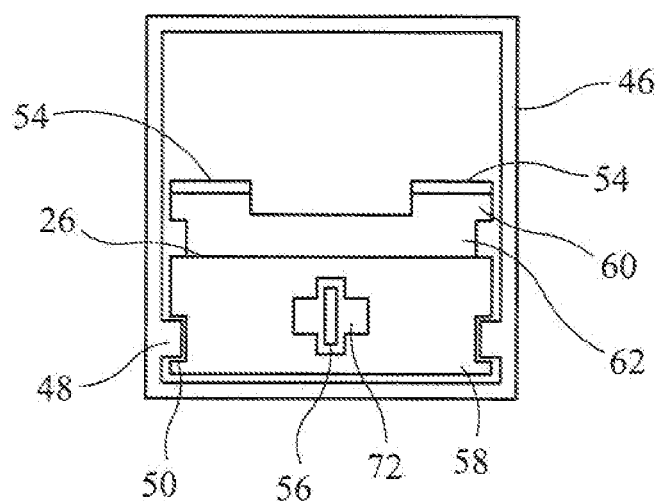
FIG. 8 is a cross-sectional view of the dispensing device of FIG. 1 taken along cut-line 8-8, showing the ratchet actuation mechanism of FIGS. 2-8.

The body 12 can also include a housing 46 for receiving the actuator 26. The actuator 26 and the body 12 can be slidably coupled. For example, the actuator 26 and can be slidably coupled to the housing 46, which is part of the body 12. The actuator 26 and the body 12 can be slidably coupled by a guide 48 and a track 50. As shown in FIG. 8, the actuator 26 and the body 12 can be slidable coupled by a guide 48, e.g., tongue, extending from each side of the housing 46 and a track 50, e.g., groove, on each lateral side of the actuator 26. Of course, this arrangement can be reversed.

Figure 11:
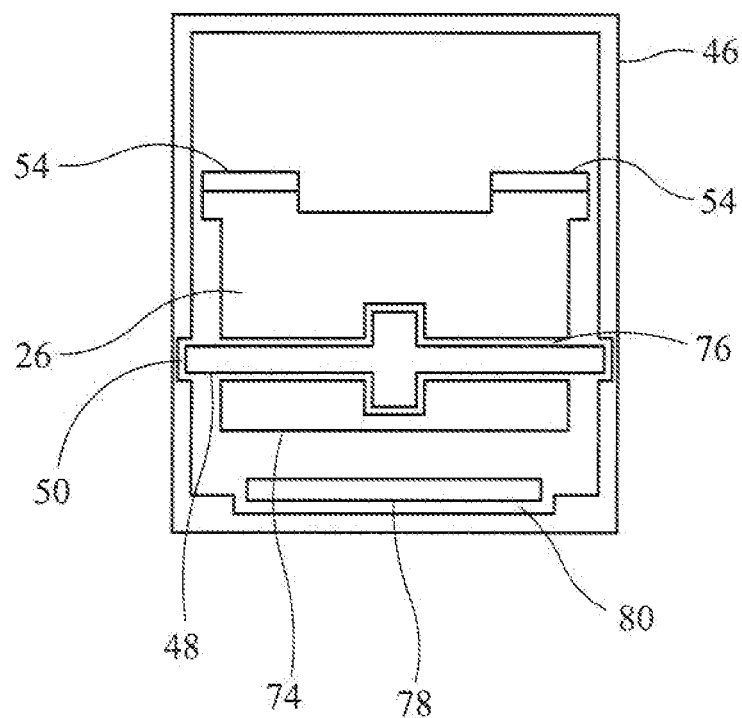
FIG. 11 is a cross-sectional view of the dispensing device of FIG. 1 taken along cut-line 8-8, showing the ratchet actuation mechanism of the secondary embodiment of FIGS. 9-10.

As shown in FIG. 11, the actuator 26 can be slidably coupled to the body 12 via a guide 48 extending through openings 76 in the actuator 26 into a track 50 in the body 12. More specifically, the actuator 26 can be slidably coupled to the housing 46 via a guide 48 extending through openings 76 in the actuator 26 into a track 50 in the body 12. In this instance, the guide 48 can be part of a distal end of the elongated linkage 28.

Each of the plungers 24 can include a ratcheted track 52 and the actuator 26 can include one or more pawl surfaces 54 adapted to engage one or more (e.g., all) of the ratcheted tracks 52 when the trigger portion 20 is pulled toward the handle 14. The dispensing device 10 can also include a pawl release lever 56 arranged such that the pawl surface(s) 54 disengage from the ratcheted track 52 when the pawl release lever 56 is actuated by a user. This enables the user to quickly slide the plungers axially. Similarly, in some instances, the plungers 24 can be designed such that they can be removed and replaced with different plungers 24 or sets thereof.

Figure 7:
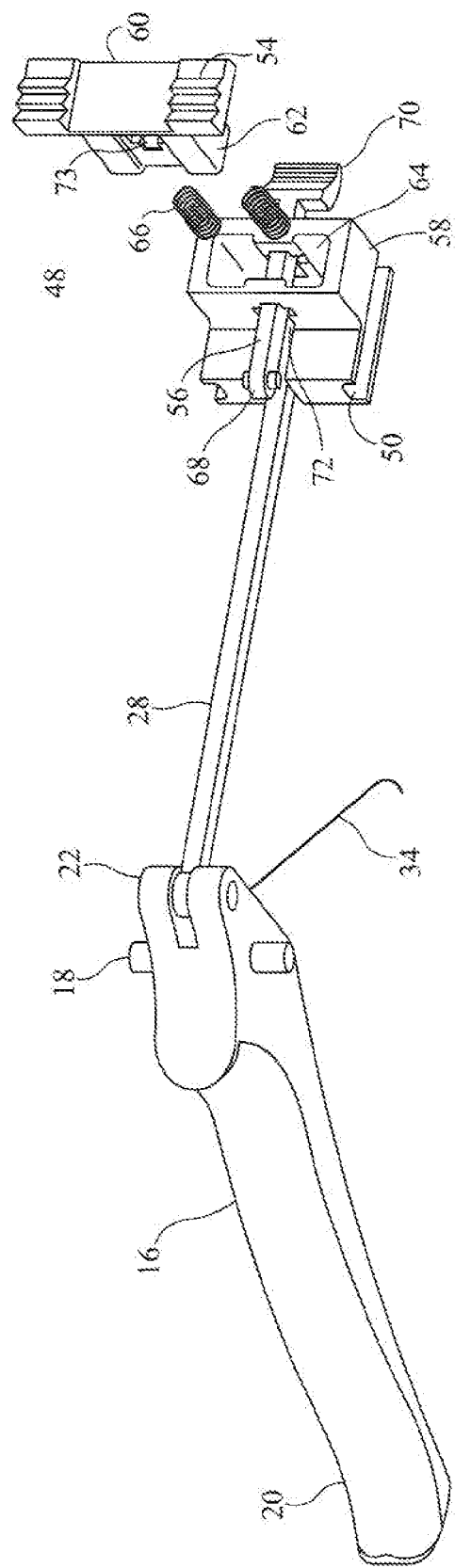
FIG. 7 is a perspective view of a ratchet actuation mechanism of the dispensing device of FIG. 2, which has been removed from the body of the dispensing device.

As shown in FIGS. 2-8, the actuator 26 can include a drive body 58 and a drive insert 60 comprising the pawl surface 54. The drive insert 60 can be compressibly coupled to the drive body 58 and upwardly biased. For example, as best shown in FIG. 7, a base 62 of the drive insert 60 can fit slidably within a receiving cavity 64 of the drive body 58.

The drive insert 60 can be compressibly coupled and upwardly biased by any material capable to biasing the drive insert 60, upward with sufficient force for the pawl surface 54 to engage the ratcheted track 52 when the pawl release lever 56 is not actuated, while the pawl surface 54 can be disengaged from the ratcheted track 52 when the pawl release lever 56 is actuated. For example, the drive insert 60 can be upwardly biased by one or more springs 66 positioned between the drive body 58 and the drive insert 60. For example, as shown in FIG. 7, two separate springs 66 can be used.

In addition to enabling the user to disengage the pawl surface 54 from the ratcheted track 52 using the pawl release lever 56, this arrangement facilitates constant interaction between the pawl surface 54 and the ratcheted track 52 when the pawl release lever 56 is not actuated. In particular, when the trigger 16 is compressed, the vertical surfaces of the pawl surface 54 interact with the vertical surfaces of the ratcheted track 52 forcing the plunger 24 forward axially. However, when the trigger 16 is released, the angled surfaces of the pawl surface 54 interact with the angled surfaces of the ratcheted track 52 to push the drive insert 60 down into the drive body 58 allowing the actuator 26 to move backward while preventing or significantly limiting backward movement of the plunger 26.

As shown in FIG. 6, in such an embodiment, a proximal end 68 of the pawl release lever 56 can be pivotably coupled to the body 12, e.g., a forward portion of the housing 46, and a distal end of the pawl release lever 56 can include a pawl release tab 70. An intermediate portion of the pawl release lever 56 can extend through an opening 72 in the drive body 58, an opening 73 in the drive insert 60, or both.

A portion of the pawl release lever 56 can extend, out of the housing 46, while another portion can be within the housing 46. For example, the pawl release tab 70 can extend out of the housing 46.

Figure 9:
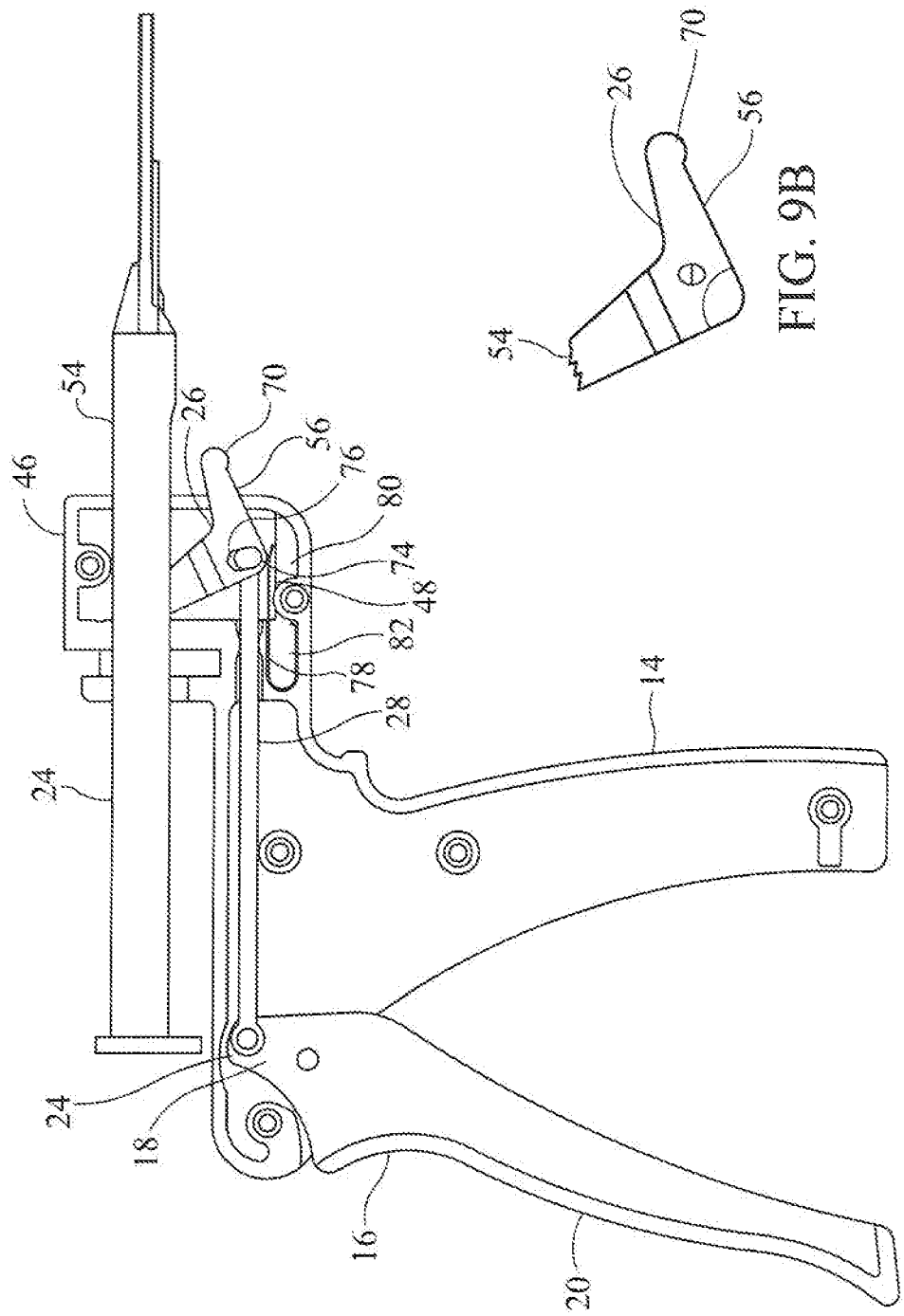
FIG. 9 is a side view of a second embodiment of the dispensing device shown in FIG. 1 with a side thereof removed.
Figure 10:
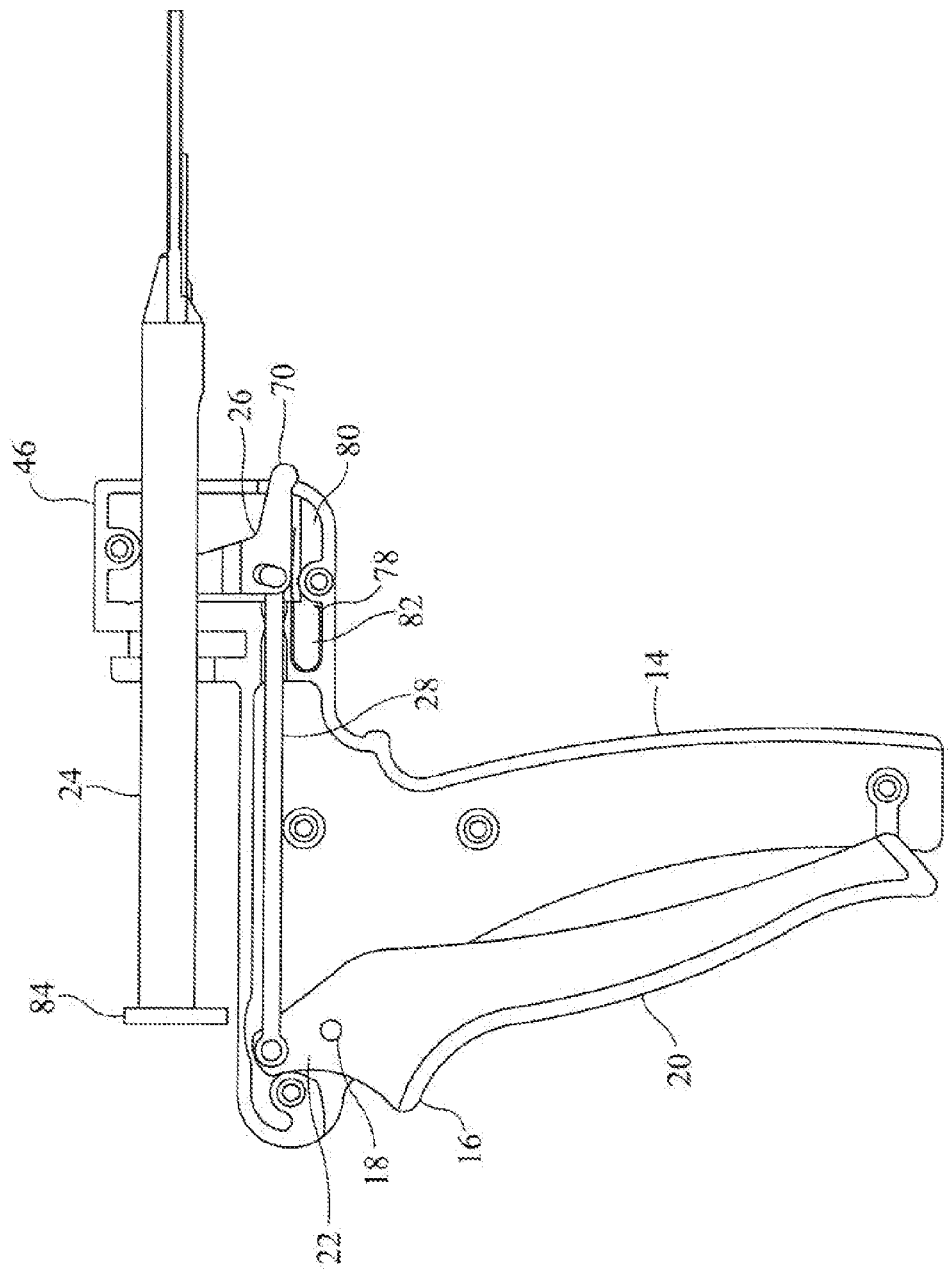
FIG. 10 is a side view of a second embodiment of the dispensing device shown in FIG. 9 with a side thereof removed and the trigger in the actuated position.

As shown in FIGS. 9-11, in another ratchet actuation mechanism, the actuator 26 can include both the pawl release lever 56 and the pawl surface(s) 54. The pawl release tab 70 can be at a first end of the actuator 26 and the pawl surface (s) 54 can be at an opposite end of the actuator 26.

As shown in FIGS. 9-11, the actuator 26 can be generally L-shaped and can be pivotably coupled to the elongated linkage 28 between the pawl release tab 70 and the pawl surface 54. More specifically, the actuator 26 can be pivotably coupled to the linkage 28 proximate the intermediate corner 74 of the L-shape. The actuator 26 can be pivotably coupled to the linkage 28 by a guide 48 extending from a distal end of the linkage 28. The guide 48 can pass through openings 76 in the actuator 26 and then slide along tracks 50 in the body 12/housing 46.

The elongated linkage 28 can be formed from a stiffened material, such as a metal, a stiff polymer or other suitable materials. As used herein, the term "stiffened" is intended to refer to a material that enables the elongated linkage to transmit rearward motion to the actuator 26 when pressure is released from the trigger 16 and the trigger 16 returns to its original position.

As used herein, "generally L-shaped" refers to a member with two legs extending from a corner. The angle ($\theta$) between the two legs can be 150° or less, or 135° or less, or 120° or less. The angle ($\theta$) between the two legs can be 60° or more, or 75° or more, or 90° or more. The angle ($\theta$) between the two legs can be 90°±30° or ±15°. For the sake of clarity, in FIG. 9B, the opening 76 is not present to best show angle ($\theta$) of actuator 26.

As shown in FIGS. 9-10, the generally L-shaped actuator 28 can be biased by an elongated spring 78 so that the pawl surface 54 engages the ratcheted track 52 unless either the actuator 28 is moving backward or the pawl release lever 56 is actuated. The elongated spring 78 can be fixed at a first end and have an opposite end extend over a deflection surface 80, which can be concave. The elongated spring 78 can be formed from a plate or strip of an elastic material, such as a metal orpolymer. The elongated spring 78 can be generally U-shaped and can have one leg of the U longer than the other. The elongated spring 78 can be fixed by insertion into a receiving cavity 82 adapted to receive the base of the U-shaped elongated spring 78 and allow the longer leg of the elongated spring 78 to extend out over the deflection surface 80.

The travel path of the actuator 26 can extend axially substantially over the deflection surface 80. The shape of the intermediate corner 74 can be adapted to achieve the desired biasing of the actuator as a result of the elongated spring 78. In particular, when the trigger 16 is pulled toward the handle 14, the vertical surfaces of the pawl surface 54 interact with the vertical surfaces of the ratcheted track 52 forcing the plunger 24 forward axially. However, when the trigger 16 is released, the angled surfaces of the pawl surface 54 interact with the angled surfaces of the ratcheted track 52 causing the actuator 26 to momentarily rotate about the guide 48 to allow the actuator 26 to move backward while preventing or significantly limiting backward movement of the plunger 26.

The invention is also drawn to a dispensing system that includes the dispensing device 10 described herein in combination with at least one elongated cartridge 40 releasably connectable to the dispensing device 10. The dispensing device 10 can include at least two plungers 24 slidably coupled to the body 12, and the at least one elongated cartridge 40 can include at least two elongated cartridges, which can be attached to one another.

The dispensing system 10 can also include a variety of replaceable plungers 24 of different sizes. For example, the dispensing system 10 can include at least two sets of plungers 24 where each set of plungers 24 has distal ends 84 of different diameters.

Bi-phase materials can be provided in cartridges 40 having different diameters that are coupled in a side-by-side arrangement. For example, some bi-phase materials are dispensed in a 1:1 ratio, while others are dispensed in a 2:3 ratio, and still others are dispensed in a 1:10 ratio. Currently, different dispensing devices are used for each of the ratios. Thus, the ability to substitute any of a variety of side-by-side plungers 24 having different size ratios can provide a substantial cost savings for dentists.

A unique aspect of the dispensing device 10 described herein is that the actuator 26, the cartridge mount 38, or both, can be positioned behind the handle 14. This arrangement is enabled, in part, by the unique ratchet actuation mechanism and allows the user to exert precision control over where the contents of a cartridge are delivered.

A device for dispensing bi-phase materials used in dental procedures is an excellent example of the benefits of this configuration. In existing dental dispensing devices, the cartridge is mounted in front of the handle portion. This results in the dispensing tip being approximately 8 inches in front of the hand of the user. In contrast, because the cartridge is mounted further back in the dispensing device 10 described herein, the dispensing tip is only 3-4 inches in from of the hand of the user, which is sufficient for the dentist to reach the back of the mouth of the patient. This difference, has substantial benefits for a dentist that include, but are not limited to:

Improved placement of the bi-phase material, which saves time and reduces waste of costly bi-phase materials and secondary syringes.

The short distance between the dispensing tip and the handle enables the dentist to brace his or her hand on the patient while dispensing the bi-phase material.

Reducing the distance between the dispensing tip and the dentist's hand, which minimizes movement at the dispensing tip when the dentist's hand becomes fatigued from procedures requiring the dentist to dispense large amounts of bi-phase materials in a short amount of time. Ratcheted delivery eliminates shaking due, to back pressure.

These benefits are particularly important toward the end of a dental procedure, particularly those procedures where large amounts of bi-phase material need to be dispensed from a cartridge in a short period of time. As will be understood, such benefits may be equally applicable to other uses, such as orthopedic surgical procedures. This is especially true where one-handed application is necessary and precise application of the contents of the cartridge is required.

The foregoing is provided for purposes of illustrating, explaining, and describing embodiments of this invention. Modifications and adaptations to these embodiments will be apparent to those skilled in the art and may be made without departing from the scope or spirit of this invention.

What is claimed is:

1. A dispensing device, comprising:
at least one plunger; a body comprising a downwardly extending, elongated handle, and a cartridge mount for receiving a cartridge to be dispensed by said at least one plunger, wherein said at least one plunger is slidably coupled to said body;
a trigger pivotably coupled to said body at a pivot point, said trigger comprising a grip portion extending downward from said pivot point and a transfer lobe extending above said pivot point;
an actuator for engaging and advancing said at least one plunger in an axial direction; and
an elongated linkage extending axially and transmitting motion from said transfer lobe to said actuator, said linkage causing said actuator to move forward axially when said trigger portion is pulled, wherein said trigger is forward of said handle, wherein said actuator is positioned axially behind said handle in an initial position, wherein said trigger is forward of said handle, wherein said transfer lobe remains below a dispensing cartridge mounted in said cartridge mount for all trigger positions.

2. The dispensing device according to claim 1, wherein said body further comprises a housing for receiving said actuator, and said actuator and said body are slidably coupled.

3. The dispensing device according to claim 2, wherein said body and said actuator are slidably coupled by a guide and a track.

4. The dispensing device according to claim 2, wherein said at least one plunger comprises a ratcheted track and said actuator further comprises a pawl surface adapted to engage said ratcheted track when said grip is pulled.

5. The dispensing device according to claim 4, further comprising a pawl release lever, wherein said pawl surface disengages from said ratcheted track when said pawl release lever is actuated.

6. The bi-phase dispending device according to claim 5, wherein said actuator comprises said pawl release lever and said pawl surface.

7. The dispensing device according to claim 6, wherein a pawl release tab is at a first end of an actuator member and said pawl surface is at an opposite end of said actuator member.

8. The dispensing device according to claim 7, wherein said actuator member is generally V-shaped and is pivotably coupled to said linkage between said pawl release tab and said pawl surface.

9. The dispensing device according to claim 8, wherein said linkage is pivotably coupled to said actuator member proximate the angel of the V-shape.

10. The dispensing device according to claim 2, wherein said actuator further comprises a drive body and a drive insert comprising a pawl surface, wherein said drive insert is compressibly and slidably coupled to said drive body and upwardly biased.

11. The dispensing device according to claim 10, further comprising a pawl release lever, wherein said pawl surface is disengaged from said ratcheted track when said pawl release lever is actuated, wherein a proximal end of said pawl release lever is pivotably coupled to said body and a distal end comprises a pawl release tab, wherein an intermediate portion of said pawl release lever extends through an opening in said drive insert.

12. The dispensing device according to claim 2, wherein a portion of said pawl release level extends out of said housing.

13. The dispensing device according to claim 1, wherein said at least one plunger comprises at least two plungers slidably coupled to said body.

14. The dispensing device according to claim 1, wherein said linkage is a rigid linkage.

15. The dispensing system according to claim 1, wherein said cartridge mount is positioned behind the handle.

16. The dispensing system according to claim 1, wherein said actuator is positioned axially behind said handle in an actuated position.

17. A dispensing system, comprising:
a dispensing device according to claim 1; and
at least one cartridge releasably connectable to said cartridge mount.

18. The dispensing system according to claim 17, wherein said dispensing device comprises at least two plungers slidably coupled to said body, and said at least one cartridge comprises at least two cartridges.

* * * * *